(12) United States Patent
Ota et al.

(10) Patent No.: US 6,764,442 B2
(45) Date of Patent: Jul. 20, 2004

(54) LIQUID AND GAS SUPPLY APPARATUS AND PORTABLE ENDOSCOPE WITH THE SAME

(75) Inventors: Noriko Ota, Saitama (JP); Shunichi Ito, Tokyo (JP)

(73) Assignee: PENTAX Corporation, Tokyo (JP)

( * ) Notice: Subject to any disclaimer, the term of this patent is extended or adjusted under 35 U.S.C. 154(b) by 106 days.

(21) Appl. No.: 10/215,293

(22) Filed: Aug. 8, 2002

(65) Prior Publication Data
US 2003/0032862 A1 Feb. 13, 2003

(30) Foreign Application Priority Data
Aug. 10, 2001 (JP) ..................................... P2001-243343

(51) Int. Cl.⁷ ................................................. A61B 1/12
(52) U.S. Cl. ..................................................... 600/158
(58) Field of Search ............................... 600/156, 157, 600/158, 159, 153, 101; 220/560.06, 565, 203.21

(56) References Cited

U.S. PATENT DOCUMENTS 4,552,130 A * 11/1985 Kinoshita ................... 600/158
4,760,838 A * 8/1988 Fukuda ....................... 600/158
5,297,537 A * 3/1994 Savitt et al. ................. 600/158
5,819,863 A * 10/1998 Zollinger et al. ............. 180/6.5
6,425,535 B1 * 7/2002 Akiba ......................... 239/369

FOREIGN PATENT DOCUMENTS

JP 08106052 4/1996

OTHER PUBLICATIONS

English Language translation for JP Appln. No. 08–106052.

* cited by examiner

Primary Examiner—Beverly M. Flanagan
(74) Attorney, Agent, or Firm—Greenblum & Bernstein, P.L.C.

(57) ABSTRACT

A portable endoscope has a pump, a tank that stores liquid, a first coupling tube that spatially connects the pump with a gas supplying tube, a divergent tube that diverges from the first coupling tube and extends toward an inside of the tank, a balloon that is spatially connected to the divergent tube and is expandable and shrinkable in the tank, a second coupling tube that spatially connects the inside of the tank with a liquid supplying tube, and a gas direction controller that selectively directs the gas discharged from the pump to one of the gas supplying tube and the divergent tube. The liquid is stored outside of the balloon. The tank includes a sealing member that hermetically seals the tank.

7 Claims, 4 Drawing Sheets

LIQUID AND GAS SUPPLY APPARATUS AND PORTABLE ENDOSCOPE WITH THE SAME

BACKGROUND OF THE INVENTION

1. Field of the Invention

The present invention relates to an endoscope with a liquid and gas supply apparatus that supplies liquid and gas such as water and air, to the tip of the endoscope.

2. Description of the Related Art

A liquid and gas supply apparatus, which has a tank and pump, is usually incorporated in a light source apparatus for a fiber-scope or an electronic endoscope system including a video-scope with an image sensor and a video-processor. In the video-scope/fiber-scope, a liquid (water) tube and a gas (air) tube are provided. The tank is spatially connected to the liquid supplying tube and the pump is spatially connected to the gas supplying tube. Generally, water is stored in the tank, whereas the pump takes in and compresses flesh air and sends the compressed air to the tip.

To wash an objective lens provided in the point of the fiber-scope/video-scope, or to remove obstructions on an observed portion, the air or water is discharged from the tip of the fiber-scope/video-scope. When supplying the air, the compressed air flows in the air tube and is then discharged from the tip of the fiber-scope/video-scope. On the other hand, when supplying the water, the compressed air is directed to the inside of the tank, where the water surface is pressed due to the pressure of the compressed gas. Consequently, the water in the tank is pumped out, and flows in the water supplying tube so that the water is discharged from the tip of the fiber-scope/video-scope.

Further, medicinal liquid for inspecting the diseased portion, nitrogen for expanding the inside of the digestive organ, and oxygen for the bronchial tubes are dischargeable via the water supplying tube or the air supplying tube.

In the case of the conventional construction of the liquid and gas supply apparatus, when the tank inclines, water can flow through the air supplying tube and can be unexpectedly discharged from the tip, hence the water is not discharged properly. Especially, the conventional liquid and gas supply apparatus mounted on a desk or table is not suitable for a portable endoscope having an internal light source, because the portablity is reduced.

SUMMARY OF THE INVENTION

Therefore, an object of the present invention is to provide a liquid and gas supply apparatus that is capable of preventing unexpected discharge of liquid, and provide a portable endoscope with the liquid and gas supply apparatus.

A liquid and gas supply apparatus according to the present invention is applied to an endoscope, and supplies liquid and gas to a liquid supplying tube and a gas supplying tube respectively. The liquid supplying tube and the gas supplying tube are provided in an endoscope (a fiber-scope or a video-scope with an image sensor). The liquid and gas supply apparatus has a pump, a tank, a first coupling tube, a divergent tube, a balloon, a second coupling tube, and a gas direction controller. The pump pumps the gas, and the tank stores the liquid. The first coupling tube spatially connects the pump with the gas supplying tube. The divergent tube diverges from the first coupling tube and extends toward the inside of the tank. The balloon is spatially connected to the divergent tube and is expandable and shrinkable in the tank. The second coupling tube spatially connects the inside of the tank with the liquid supplying tube such that the liquid in the tank flows in the second coupling tube. The gas direction controller selectively directs the gas discharged from the pump to either the gas supplying tube or the divergent tube. For example, a switch button for performing the gas-supply and the liquid-supply is provided on the endoscope, and a flow-controlling member (for example, a valve) that selectively directs the gas to the gas supplying tube or the divergent tube, is connected to the switch button.

In the present invention, the liquid is stored outside the balloon, and the balloon is constructed such that the liquid outside the balloon does not penetrate to the balloon. The tank includes a sealing member that hermetically seals the tank except for the second coupling tube and the divergent tube. When the gas is supplied, the gas flows in the first coupling tube and the gas supplying tube so that the gas is discharged from the tip of the endoscope. On the other hand, when the liquid is supplied, the gas is directed to the inside of the balloon via the divergent tube by the gas direction controller. The balloon expands due to the input of gas, and the liquid in the tank is pressed because the tank is sealed hermetically. Consequently, the liquid flows in the second coupling tube and is discharged from the tip of the endoscope. Since the liquid does not pass through the balloon, the liquid does not flow into the first coupling tube and the gas supplying tube. Thus, the liquid is not erratically discharged from the tip of the endoscope.

For example, the gas is air and the liquid is water. In this case, preferably, the pump takes in flesh air and discharges compressed air. The compressed air directed to the balloon to expand the balloon. The balloon is expandable and shrinkable. For example, the balloon is composed of a rubber elastic member.

A liquid and gas supply apparatus according to another aspect of the present invention has a pump, a tank, a first coupling tube, a divergent tube, a balloon, a second coupling tube, and a gas direction controller. The pump pumps the gas, and the tank stores the liquid. The first coupling tube spatially connects the pump with the gas supplying tube. The divergent tube diverges from the first coupling tube and extends toward an inside of the tank. The second coupling tube spatially connects the inside of the tank with the liquid supplying tube. The balloon is spatially connected to the second coupling tube and is expandable and shrinkable in the tank. The gas direction controller selectively directs the gas discharged from the pump to one of the gas supplying tube and the divergent tube. The tank includes a sealing member that hermetically seals the tank except for the second coupling tube and the divergent tube. In the present invention, the liquid is stored inside the balloon. When the gas is supplied, the gas flows in the first coupling tube and the gas supplying tube so that the gas is discharged from the tip of the endoscope. On the other hand, when the liquid is supplied, the gas is directed to the inside of the balloon via the divergent tube by the gas direction controller. The balloon shrinks due to the increased gas-pressure, and the balloon is pressed because the tank is sealed hermetically. Consequently, the liquid flows in the second coupling tube and is discharged from the tip of the endoscope.

A portable endoscope according to another aspect of the present invention has a gas supplying tube that transmits gas to discharge the gas from a tip of the endoscope, a liquid supplying tube that transmits liquid to discharge the liquid from the tip of the endoscope, a pump that pumps the gas, a tank that stores the liquid, a first coupling tube that spatially connects the pump with the gas supplying tube, a divergent tube that diverges from the first coupling tube and extends toward an inside of the tank, a balloon that is spatially connected to the divergent tube and is expandable and shrinkable in the tank, a second coupling tube that spatially connects the inside of the tank with the liquid supplying tube such that the liquid in the tank flows in the second coupling tube, and a gas direction controller that selectively directs the gas discharged from the pump to one of the gas supplying tube and the divergent tube. The liquid is stored outside the balloon. The tank includes a sealing member that hermetically seals the tank except for the second coupling tube and the divergent tube.

A portable endoscope according to another aspect of the present invention has a gas supplying tube that transmits gas to discharge the gas from a tip of the endoscope, a liquid supplying tube that transmits liquid to discharge the liquid from the tip of the endoscope, a pump that pumps the gas, a tank that stores the liquid, a first coupling tube that spatially connects the pump with the gas supplying tube, a divergent tube that diverges from the first coupling tube and extends toward an inside of the tank, a second coupling tube that spatially connects the inside of the tank with the liquid supplying tube, a balloon that is spatially connected to the second coupling tube and is expandable and shrinkable in the tank, a gas direction controller that selectively directs the gas discharged from the pump to one of the gas supplying tube and the divergent tube. The liquid is stored inside the balloon, and the tank includes a sealing member that hermetically seals the tank except for the second coupling tube and the divergent tube.

A liquid and gas supply apparatus according to another aspect of the present invention has a container that stores liquid, a space divider that divides an inside space of the container into a first space for storing the liquid and a second space such that one of the first space and the second space expands while the other shrinks, a gas transmitting tube that extends to the second space, a liquid transmitting tube that spatially connects the first space with the liquid supplying tube, and a liquid and gas supplier that supplies the gas to the gas supplying tube, and supplies the liquid in the first space to the liquid supplying tube by supplying the gas to the second space and expanding the second space.

A portable endoscope according to another aspect of the present invention has a gas supplying tube that transmits gas to discharge the gas from a tip of the endoscope, a liquid supplying tube that transmits liquid to discharge the liquid from the point of the endoscope, a container that stores liquid, a space divider that divides an inside space of the container into a first space for storing the liquid and a second space such that one of the first space and the second space expands while the other shrinks, a gas transmitting tube that extends to the second space, a liquid transmitting tube that spatially connects the first space with the liquid supplying tube, and a liquid and gas supplier that supplies the gas to the gas supplying tube, and supplies the liquid in the first space to the liquid supplying tube by supplying the gas to the second space and expanding the second space.

BRIEF DESCRIPTION OF THE DRAWINGS

The present invention will be better understood from the description of the preferred embodiment of the invention set fourth below together with the accompanying drawings, in which.

DESCRIPTION OF THE PREFERRED EMBODIMENTS

Hereinafter, the preferred embodiments of the present invention are described with reference to the attached drawings.

Figure 1:
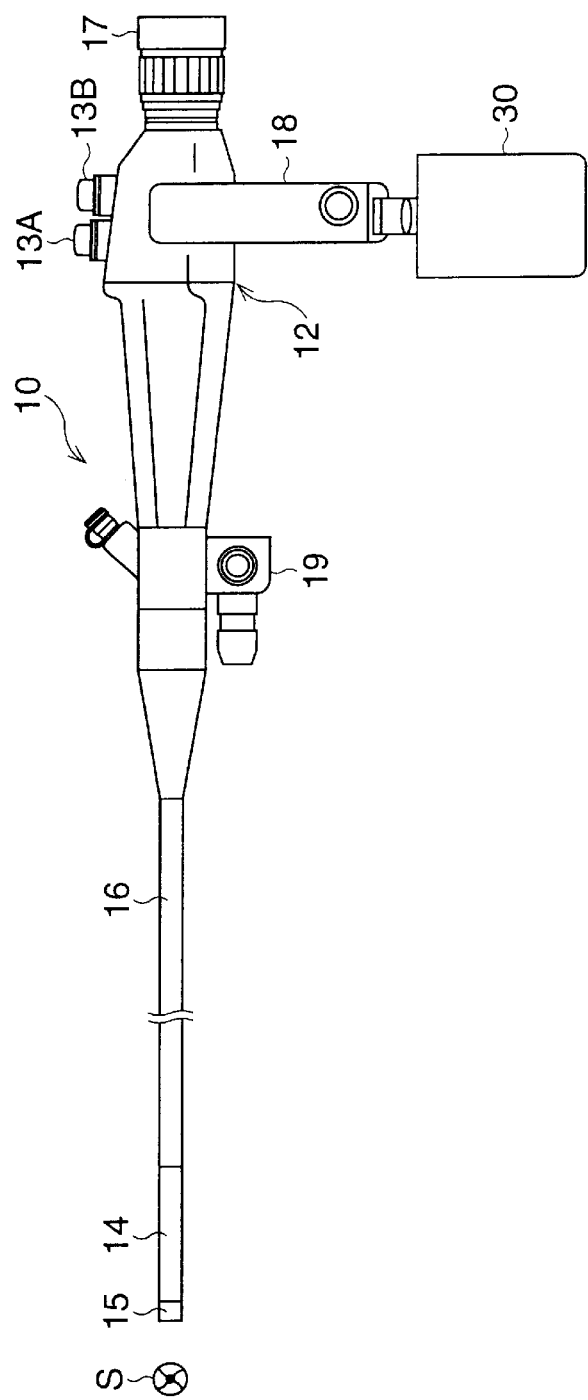
FIG. 1 is a schematic plan view of portable endoscope according to a first embodiment.

FIG. 1 is a schematic plan view of a portable endoscope according to the first embodiment.

A fiber-scope 10 is a portable type fiber-scope with an internal light source, and has a tip portion 15, a bending portion 14, an inserting portion 16, an operating portion 12, an eyepiece 17, a light source unit 19, and a connecting arm 18. Further, the fiber-scope 10 has a water and air supplying apparatus, as described later. When an operation or inspection is started, the inserting portion 16 is inserted into an inner organ, such as the stomach.

A lamp (not shown) for illuminating a subject S is provided in the light source unit 19. A fiber-optic bundle (not shown) is provided in the fiber-scope 10 and extends from the light source unit 19 to the tip portion 15. Light radiated from the lamp passes through the fiber-optic bundle and is radiated from the tip portion 15. Consequently, the subject S is illuminated by the radiated light. Light reflected on the subject S passes through an objective lens (not shown) provided in the tip portion 15, and reaches an incident surface of an image fiber-optic bundle (not shown). Thus, the subject image is formed on the incident surface. The image fiber-optic bundle is provided for optically transmitting the subject image and extends from the tip portion 15 to the eyepiece 17. The optically transmitted subject image is formed at the eyepiece, thus the operator can observe the subject S via the eyepiece 17.

A lever (not shown) for bending the bending portion 15, and a water and air supplying switch button 13A, and a lamp switch button 13B are provided on the operating portion 12. The water and air supplying switch button 13A is operated to supply the water and the air, as described later. A tank 30, in which water is stored, is detachably attached to the connecting arm 18 extending from the operating portion 12.

Figure 2:
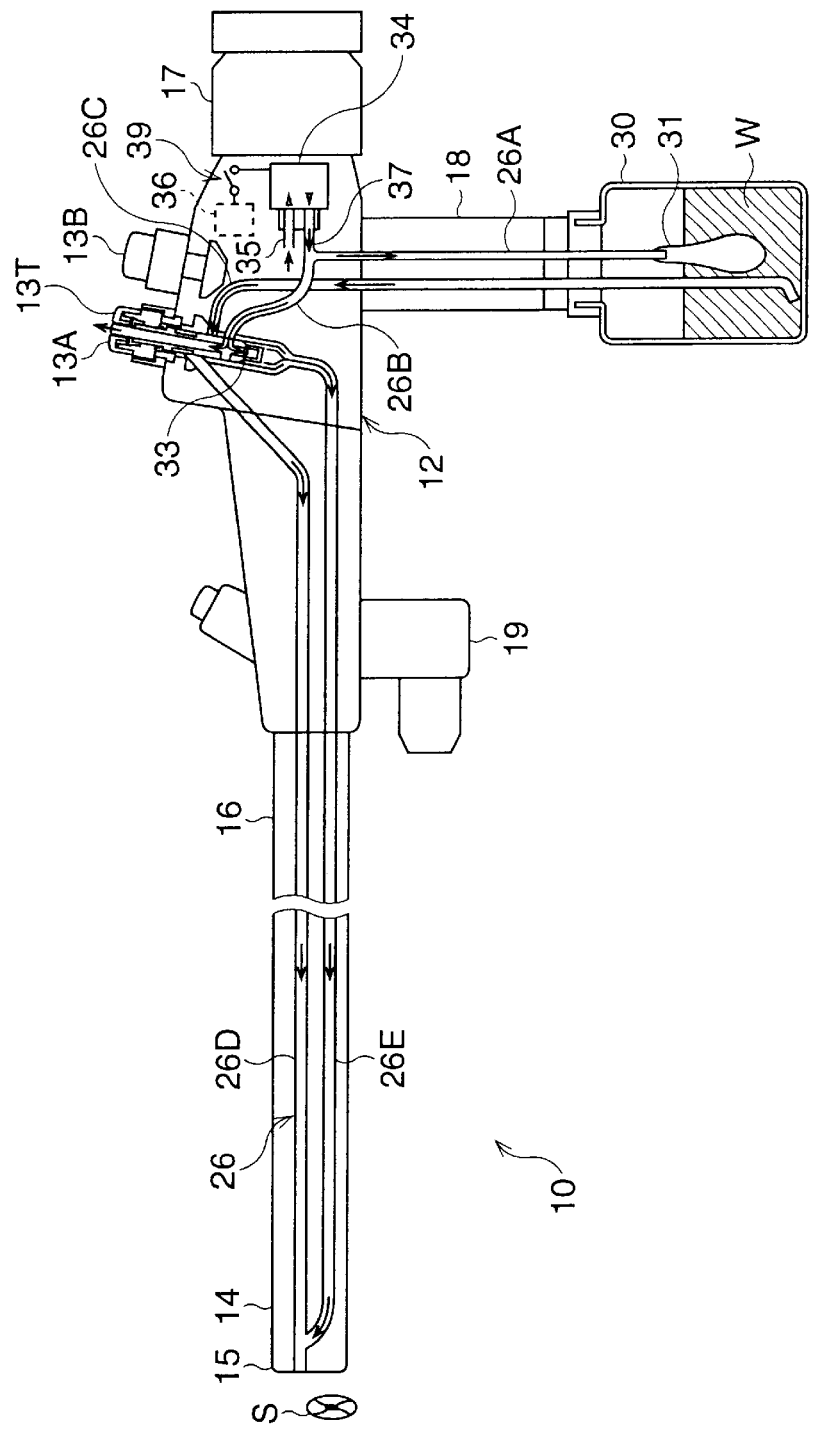
FIG. 2 is a view schematically showing an inner construction of the fiber-scope.

FIG. 2 is a view schematically showing an inner construction of the fiber-scope 10.

To wash the objective lens and remove a dart on the subject S, water and air supplying tubes 26 are provided in the fiber-scope 10. The water and air supplying tubes 26 has an air supplying tube 26E for transmitting air, and a liquid supplying tube 26D for transmitting water. They extend from the tip portion 15 to the water and air supplying switch button 13A. A pump 34 is provided in the operating portion 12, and a coupling tube 26B is provided between the pump 34 and the water and air supplying switch button 13A to spatially connect the pump 34 with the air supplying tube 26E. A divergent tube 26A, which diverges from the coupling tube 26B, extends to the inside of the tank 30, and a balloon 31 is attached to the point of the divergent tube 26A. On the other hand, a coupling tube 26C is provided between the tank 30 and the water and air supplying switch button 13A to spatially connect the inside of the tank 30 with the water supplying tube 26D.

The pump 34 takes in flesh air and discharges compressed air, and the an intake tube 35 extends to a hole (not shown) formed on an outer surface of the operating portion 12. A discharging outlet 37, from which the compressed air is discharged, is spatially connected to the coupling tube 26B and the divergent tube 26A. When the pump 34 operates, the compressed air flows in the coupling tube 26B toward the water and air supplying switch button 13A. Electric power is supplied from a battery 36 to the pump 34. When a pump button (not shown) is operated, a pump switch 39 provided between the battery 36 and the pump 34 is turned ON, thus the pump 34 operates.

A valve 33 is connected to the water and air supplying switch button 13A. When the water and air supplying switch button 13A is not covered by the thumb of the operator, the valve 33 intercepts, or closes the spatial connection between the coupling tube 26B and the air supplying tube 26E, and discharges the compressed air, transmitted from the pump 34, from the top portion 13T of the water and air supplying switch button 13A. In other words, the compressed air is not supplied to the air supplying tube 26E, hence air is not supplied. Further, the valve 33 closes the spatial connection between the water supplying tube 26D and the water coupling tube 26C, hence water is not supplied.

When supplying air, the thumb of the operator is placed on the top portion 13T of the water and air supplying switch button 13A. The position of the valve 33 is shifted toward the opposite side of the top portion 13A by the backflow of air, so that the coupling tube 26B is spatially connected to the air supplying tube 26E. Thus, the compressed air is fed from the pump 34 to the air supplying tube 26E and is discharged from the tip portion 15.

When supplying water, the water and air supplying switch button 13A is pressed by the thumb of the operator. The position of the valve 33 is further shifted by the pressing, which spatially closes the coupling tube 26B and the air supplying tube 26E, and spatially connects the coupling tube 26C and the water supplying tube 26D. Consequently, as described later, the compressed air from the pump 34 flows toward the tank 30, and the water W in the tank 30 is displaced. The displaced water W flows in the coupling tube 26C, the water and air supplying switch button 13A, and the water supplying tube 26D, and is then discharged from the tip portion 15.

Note that, the construction of the water and air supplying switch button 13A having the valve 33, described above, is well known in the prior art.

Figure 3A:
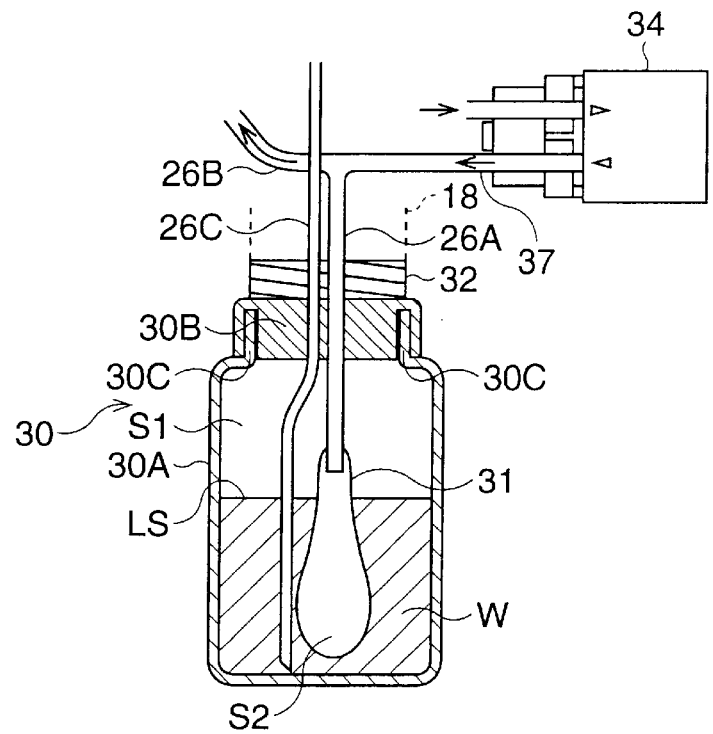
FIGS. 3A and 3B are views showing the flow of air and water.
Figure 3B:
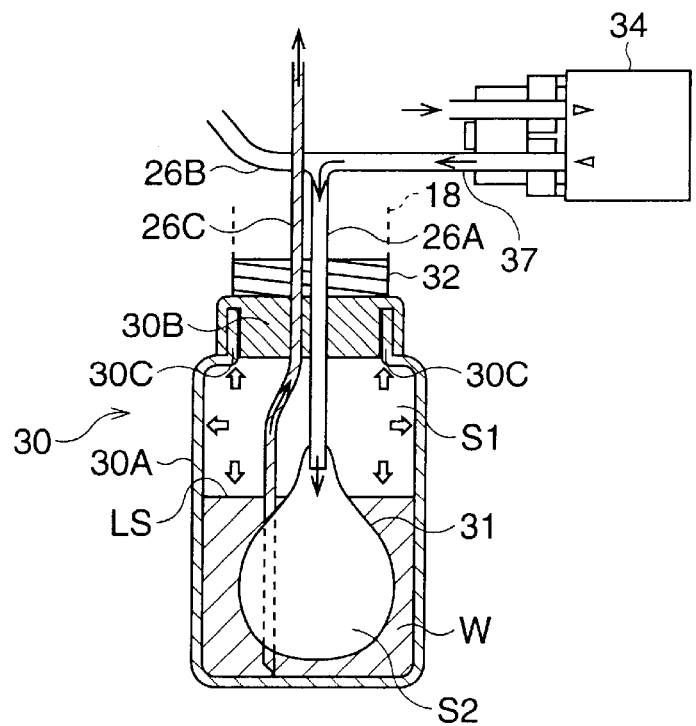

FIGS. 3A and 3B are views showing a flow of air and water.

The cylindrical tank 30 has a storing portion 30A, a cover 30B and connecting portion 32, the connecting portion 32 being attached at the upper surface of the cover 30B. The coupling tube 26C and the divergent tube 26A respectively go through the connecting portion 32 and the cover 30B, and extend to the inside of the tank 30. The connecting portion 32 has a male screw configuration and is thread into the connecting arm 18. Namely, the tank 30 is detached from the connecting arm 18 by rotating the tank 30. The cover 30B is attached to the storing portion 30A such that the cover 30B interposes the ring-shaped upper edge 30C of the storing portion 30A. The storing portion 30A is detachable from the cover 30B by pulling the storing portion 30A downward, namely, away from the connecting arm 18. When adding the water W, the storing portion 30A is detached form the cover 30B. The cover 30B hermetically seals the inside of the storing portion 30A. While the storing portion 30A is attached to the cover 30B, the air and water W in the tank 30 do not leak out and no gas or liquid penetrates into the tank 30, except through the coupling tube 26C and the divergent tube 26A.

In this embodiment, the balloon 31 is composed of a rubber elastic compound, which is impervious to liquid. When the compressed air is fed from the pump 34 to the balloon 31, the balloon 31 expands, namely, inside space of the balloon 31 increases. On the other hand, when compressed air is not fed, the balloon 31 is maintained in the shrunk situation. In the tank 30, the water W is stored outside the balloon 31, and the amount of water W is a half of the capacity of the tank 30. Hereinafter, the space, in which the water W is stored, is designated as the "first space", and the space in the balloon 31 is designated as the "second space".

When supplying the air, the compressed air discharged from the pump 34 flows in the coupling tube 26B and is directed to the water and air supplying switch button 13A and the air supplying tube 26E. Therefore, the water W does not flow out from the tank 30 and the balloon 31 does not expand (See FIG. 3A).

When the water and air supplying switch button 13A is pressed to supply the water, the compressed air discharged from the pump 34 flows in the divergent tube 26A, so that the balloon 31 expands. The liquid surface LS of the water W tends to rise because of the expansion of the balloon 31. However, since the tank 30 is sealed hermetically by the cover 30B, air pressure in the first space S1 increases, which presses the liquid surface LS of the water W downward. Consequently, the water W flows in the coupling tube 26C and is discharged from the tip portion 15 via the water and air supplying switch button 13A and the water supplying tube 26D (See FIG. 3B). The amount of the water W, which is supplied, corresponds to expanded volume of the balloon 31. When the pump 34 is suspended after the balloon 31 expands, the balloon 31 shrinks and pressure in the first space S1 decreases. Consequently, the situation in the tank 30 returns to the situation before the water-supply.

In this way, in this embodiment, the balloon 31 is provided in the tank 30 and is connected to the tip of the coupling tube 26B. The water W is stored in the first space S1 and the cover 30B seals hermetically the storing portion 30A. When the compressed air is fed to the balloon 31, the water W is forced out by pressure and flows in the coupling tube 26C because of the expansion of the balloon 31. In this embodiment, the path for the water and the path for the air are perfectly separate. Therefore, although the tank 30 inclines while the endoscope 10 is being operated, the water W is not erratically discharged from the tip portion 15 via the air supplying tube 26E.

Since the balloon 31 shrinks when the pump 34 is suspended, the water W is not instantaneously discharged when the storing portion 30A is detached from the cover 30B.

The balloon 31 may be composed of material other than rubber elastic, if expandable and shrinkable. The coupling tube 26C may be arranged adjacent to the storing portion 30A so that the coupling tube 26C dose not interfere with the expanded balloon 31.

In this embodiment, the water-supply and the air-supply are independently controlled by using the water and air supplying switch button 13A with the valve 33. However, other construction may be applied. For example, the flow of the compressed air may be controlled by a solenoid valve.

As for the construction of the tank 30, a member other than the cover 30B can be used to seal the inside of the tank 30 hermetically. Further, the tank 30 may be attached to the connecting arm 18 such that the water surface LS of the water W is perpendicular to a line passing through the tip portion 15 and eyepiece 17.

Figure 4A:
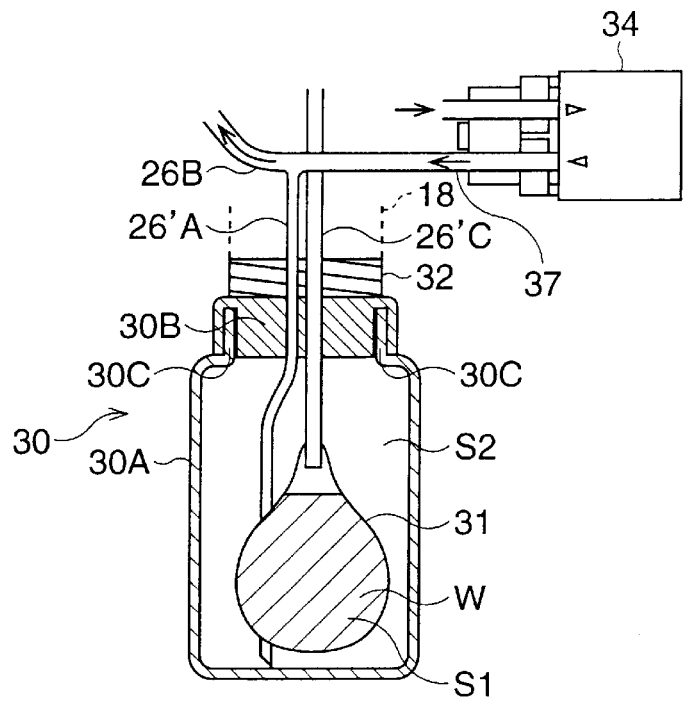
FIGS. 4A and 4B are views showing the flow of air and water according to the second embodiment.
Figure 4B:
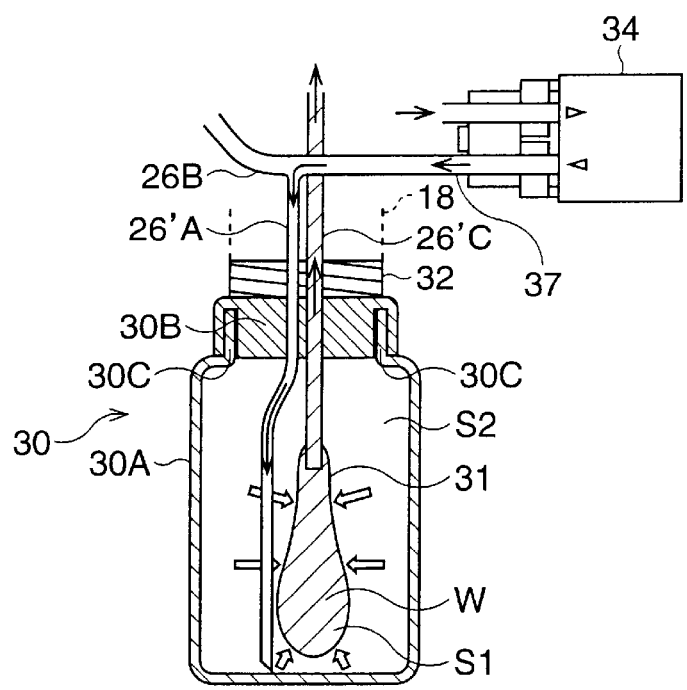

FIGS. 4A and 4B are views showing the flow of water and air according to a second embodiment. The second embodiment is different from the first embodiment in that water is stored in a balloon.

As shown in FIG. 4A, in the second embodiment, the balloon 31 is attached to the coupling tube 26'C (not the divergent tube), and the divergent tube 26'A extends to the bottom of the tank 30. The water W is stored in the space inside of the balloon 31 (in the second embodiment, designated as the "first space"), and is not stored in the space outside of the balloon 31 (in the second embodiment, designated as the "second space").

When supplying the air, the compressed air discharged from the pump 34 directly flows in the coupling tube 26B and is discharged from the tip portion 15. On the other hand, when supplying the water, the compressed air flows in the divergent tube 26'A and is directed to the inside of the tank 30. The pressure in the second space S2 increases because of the inflow of the compressed air. The balloon 31 shrinks as the second space S2 expands, so that the water W flows through the coupling tube 26'C and is discharged from the tip portion 15.

In the first and second embodiments, the water and air supplying apparatus is incorporated in the portable fiberscope 10, however, the water and air supplying apparatus may be applied to a conventional light source or electronic endoscope mounted on a desk or table.

As for the air-supply, nitrogen or oxygen may be discharged from the tip portion 15 in place of air. In this case, a nitrogen cylinder or oxygen cylinder may be connected to the inlet of the pump 34. Further, as for the water-supply, medicinal liquid maybe stored in the tank 30 in place of water.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No. 2001-243343 (filed on Aug. 10, 2001) which is expressly incorporated herein, by reference, in its entirety.

What is claimed is:

1. A liquid and gas supply apparatus for supplying liquid and gas to a liquid supplying tube and a gas supplying tube, provided in an endoscope, said liquid and gas supply apparatus comprising:
   a pump that pumps the gas;
   a tank that stores the liquid;
   a first coupling tube that spatially connects said pump with said gas supplying tube;
   a divergent tube that diverges from said first coupling tube and extends toward an inside of said tank;
   a balloon that is spatially connected to said divergent tube and is expandable and shrinkable in said tank, the liquid being stored outside of said balloon;
   a second coupling tube that spatially connects the inside of said tank with said liquid supplying tube such that the liquid in said tank flows in said second coupling tube; and
   a gas direction controller that selectively directs the gas discharged from said pump to one of said gas supplying tube and said divergent tube,
   wherein said tank includes a sealing member that hermetically seals said tank except for said second coupling tube and said divergent tube.

2. A liquid and gas supply apparatus for supplying liquid and gas to a liquid supplying tube and a gas supplying tube, provided in an endoscope, respectively, said liquid and gas supply apparatus comprising:
   a pump that pumps the gas;
   a tank that stores the liquid;
   a first coupling tube that spatially connects said pump with said gas supplying tube;
   a divergent tube that diverges from said first coupling tube and extends toward an inside of said tank;
   a second coupling tube that spatially connects the inside of said tank with said liquid supplying tube;
   a balloon that is spatially connected to said second coupling tube and is expandable and shrinkable in said tank, the liquid being stored inside of said balloon; and
   a gas direction controller that selectively directs the gas discharged from said pump to one of said gas supplying tube and said divergent tube,
   wherein said tank includes a sealing member that hermetically seals said tank except for said second coupling tube and said divergent tube.

3. The liquid and gas supply apparatus of claim 1, wherein the balloon is composed of rubber elastic.

4. A portable endoscope comprising:
   a gas supplying tube that transmits gas to discharge the gas from a tip of said endoscope;
   a liquid supplying tube that transmits liquid to discharge the liquid from the tip of said endoscope;
   a pump that pumps the gas;
   a tank that stores the liquid;
   a first coupling tube that spatially connects said pump with said gas supplying tube;
   a divergent tube that diverges from said first coupling tube and extends toward an inside of said tank;
   a balloon that is spatially connected to said divergent tube and is expandable and shrinkable in said tank, the liquid being stored outside of said balloon;
   a second coupling tube that spatially connects the inside of said tank with said liquid supplying tube such that the liquid in said tank flows in said second coupling tube; and
   a gas direction controller that selectively directs the gas discharged from said pump to one of said gas supplying tube and said divergent tube,
   wherein said tank includes a sealing member that hermetically seals said tank except for said second coupling tube and said divergent tube.

5. A portable endoscope comprising:
   a gas supplying tube that transmits gas to discharge the gas from a tip of said endoscope;
   a liquid supplying tube that transmits liquid to discharge the liquid from the tip of said endoscope;
   a pump that pumps the gas;
   a tank that stores the liquid;
   a first coupling tube that spatially connects said pump with said gas supplying tube;
   a divergent tube that diverges from said first coupling tube and extends toward an inside of said tank;
   a second coupling tube that spatially connects the inside of said tank with said liquid supplying tube;
   a balloon that is spatially connected to said second coupling tube and is expandable and shrinkable in said tank, the liquid being stored inside of said balloon; and a gas direction controller that selectively directs the gas discharged from said pump to one of said gas supplying tube and said divergent tube, wherein said tank includes a sealing member that hermetically seals said tank except for said second coupling tube and said divergent tube.

6. A liquid and gas supply apparatus for supplying liquid and gas to a liquid supplying tube and a gas supplying tube, provided in an endoscope, said liquid and gas supply apparatus comprising:

a container that stores liquid;

a space divider that divides an inside space of said container into a first space for storing the liquid and a second space such that one of said first space and said second space expands while the other shrinks;

a gas transmitting tube that extends to said second space;

a liquid transmitting tube that spatially connects said first space with said liquid supplying tube; and a liquid and gas supplier that supplies the gas to said gas supplying tube, and supplies the liquid in said first space to said liquid supplying tube by supplying the gas to said second space and expanding said second space.

7. A portable endoscope comprising:

a gas supplying tube that transmits gas to discharge the gas from a tip of said endoscope;

a liquid supplying tube that transmits liquid to discharge the liquid from the tip of said endoscope;

a container that stores liquid;

a space divider that divides an inside space of said container into a first space for storing the liquid and a second space such that one of said first space and said second space expands while the other shrinks;

a gas transmitting tube that extends to said second space;

a liquid transmitting tube that spatially connects said first space with said liquid supplying tube; and a liquid and gas supplier that supplies the gas to said gas supplying tube, and supplies the liquid in said first space to said liquid supplying tube by supplying the gas to said second space and expanding said second space.

* * * * *